US010492391B2

(12) United States Patent
Deneer et al.

(10) Patent No.: US 10,492,391 B2
(45) Date of Patent: Dec. 3, 2019

(54) METHODS FOR BREEDING SHORT CELERY

(71) Applicant: RIJK ZWAAN ZAADTEELT EN ZAADHANDEL B.V., De Lier (NL)

(72) Inventors: Reinier Hendrik Marie Deneer, De Lier (NL); Grit Anja Glawe, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days.

(21) Appl. No.: 15/697,622

(22) Filed: Sep. 7, 2017

(65) Prior Publication Data
US 2017/0367283 A1    Dec. 28, 2017

Related U.S. Application Data

(63) Continuation of application No. 13/798,352, filed on Mar. 13, 2013, now abandoned.

(30) Foreign Application Priority Data

Mar. 22, 2012 (EP) ..................... 12160783

(51) Int. Cl.
A01H 1/00      (2006.01)
A01H 6/06      (2018.01)
A01H 5/04      (2018.01)
A01H 5/00      (2018.01)
A01H 5/12      (2018.01)

(52) U.S. Cl.
CPC ............... A01H 1/00 (2013.01); A01H 5/00 (2013.01); A01H 5/04 (2013.01); A01H 5/12 (2013.01); A01H 6/064 (2018.05)

(58) Field of Classification Search
None
See application file for complete search history.

(56) References Cited

U.S. PATENT DOCUMENTS

2006/0253941 A1* 11/2006 Trammell ............... A01H 5/12
                                                        800/318
2008/0092257 A1*  4/2008 Davie ..................... A01H 5/10
                                                        800/320.1

OTHER PUBLICATIONS

Paul et al. Gamma-rays and EMS induced macromutants in celery (Apium graveolens L.), fennel )Foeniculum vulgare Mill.) and ajawan (Trachyospermum amni L.). (2005) J. of Phytological Research; vol. 18; pp. 95-98 (Year: 2005).*
Appell, S. D. The potted garden: new plants and new approaches for container gardens. (2001) in Brooklyn Botanic Garden publications; pp. 80-86 (Year: 2001).*
Noguchi et al. Brassinosteroid-insensitive dwarf mutants of Arabidopsis accumulate brassinosteroids. (1999) Plant Physiology; vol. 121; pp. 743-752 (Year: 1999).*
Richards et al. How gibberellin regulates plant growth and development: a molecular genetic analysis of gibberellin signaling.(2001) Annu. Rev. Plant Physiol. Plant Mol. Biol.; vol. 552; pp. 67-88 (Year: 2001).*
Steber et al. Isolation of the GA-response mutant sly1 as a suppressor of ABI1-1 in Arabidopsis thaliana. (1998) Genetics; vol. 149; pp. 509-521 (Year: 1998).*
"American Agriculturist for the Farm, Garden, and Household", vol. XXV, No. 2, Feb. 1866.
Appell. "The potted garden: new plants and new approaches". (2001) Brooklyn Botanic Garden publications; pp. 80-86.
Barr & Sons, "Barr's Seed Guide", 1906.
Binkley. "Celery production in Colorado", 1934, Colorado Agric. Exp. Sta. Bulletin, 407:1-32.
Binkley et al. "Strain of giant pascal celery resistant to "Yellows" is being developed at Station", 1945 Colorado Farm Bulletin, 7: 3-4.
Folia. "Celery 'Giant Pascal'", 2016, downloaded from the world wide web at myfolia.com; pp. 1-3.
Gardening Illustrated, No. 821, vol. XVI, Dec. 1, 1894.
Hancock, et al. "A horticultural trinity—carnations, celery, tomatoes", 1937, Proceedings of the summer meeting of the state horticultural society of Michigan state; pp. 52-53.
Hazard. "The Channel Islands: People and Their Cattle", 1881.
Hessayon. "The Vegetable & Herb Expert", 2003, pp. 47-49.
Maroto et al. "Posibilidades de produccion primaveral tardia con diversas modalidades de forzado o semiforzado en el cultivo del apio (Apium graveolens L. var. "Dulce" [Mill.] Pers.) en el litoral mediterraneo espanol", 1988, Investigacion Agraria produccion y Proteccion Vegetales, 3:163-180.
Noguchi, et al. "Brassinosteroid-insensitive dwarf mutants of Arabidopsis accumulate brassinosteroids" Nov. 1999, Plant Physiology; 121:743-752.
Nonnecke. "Vegetable Production", 1989, pp. 488-489.
Paul, et al. "Gamma-rays and EMS induced macromutants in celery (Apium graveolens L.), fennel (Foeniculum vulgare Mill.) and ajawan (Trachyospermum amni L.)", 2005, J. of Phytological Research, 18:95-98.
Pressman et al. "Interaction of daylength and applied gibberellins on stem growth and leaf production in three varieties of celery", 1987, J. of Exp. Botany; 38:968-971.

(Continued)

Primary Examiner — Cathy Kingdon Worley
(74) Attorney, Agent, or Firm — Duane Morris LLP; Thomas J. Kowalski; Deborah L. Lu

(57) ABSTRACT

The present invention relates to a celery plant (Apium graveolens L. dulce) carrying a genetic trait that leads to a shorter petiole and a shorter total plant length at mature harvest stage as compared to a celery plant not carrying the said genetic trait, wherein said genetic trait is as present in the genome of plants grown from seed of which a representative sample was deposited with the NCIMB under accession number NCIMB 41902.

3 Claims, 2 Drawing Sheets

(56) References Cited

OTHER PUBLICATIONS

Richards, et al. "How gibberellin regulates plant growth and development: a molecular genetic analysis of gibberellin signaling", 2001, Annu. Rev. Plant Physiol. Plant Mol. Biol.; 52:67-88.
The Rural New-Yorker, vol. LXXIL, No. 4137, Jan. 25, 1913.
Seedaholic.com "Celery 'Golden Self Blanching' Seeds" (2016) downloaded from the world wide web at seedaholic.com; pp. 1-6.
Steber, et al. "Isolation of the GA-response mutant sly1 as a suppressor of ABI1-1 in *Arabidopsis thaliana*", Jun. 1998, Genetics; vol. 149:509-521.
Weaver. "Heirloom Celery Varieties", Apr. 24, 2013.
West. "Practical Gardening for Indian Amateurs", 1892, pp. 147-149.
"Yearbook of Agriculture" 1937, pp. 334-335.

\* cited by examiner

Leaf: length (including petiole) (8)
Leaf: distance between 1st and 2nd pair of leaflets (9)
Leaf: size of the terminal leaflet (10)
Petiole: length (16)
width (17)

METHODS FOR BREEDING SHORT CELERY

RELATED APPLICATIONS AND INCORPORATION BY REFERENCE

This application is a continuation of U.S. application Ser. No. 13/798,352 filed on Mar. 13, 2013, now pending, which claims priority to EP patent application Ser. No. 12160783.2 filed 22 Mar. 2012.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a new type of celery (*Apium graveolens* L. *dulce*). The invention further relates to seeds of the plant and to propagation material for the plant and progeny of the plant.

BACKGROUND OF THE INVENTION

*Apium graveolens* is a plant species belonging to the Apiaceae family, which comprises two important vegetable crops, namely celery and celeriac. In *Apium graveolens* L. *dulce* (celery, also known as stalk celery) the plant part that is typically harvested for consumption is the petiole. The petiole carries a leaf blade, and a petiole and its leaf blade together form a leaf of the celery plant. Typically, celery plants comprise multiple leaves. The leaves of celery are compound leaves that are composed of a petiole or leaf stem, and a fully subdivided leaf blade. The leaf blade consists of several pairs of leaflets and ends in a terminal leaflet.

A single celery plant typically represents a large amount of biomass, and for some market segments this is often a too large portion for the consumer. Celery is a vegetable that has a relatively large amount of unusable parts. On average 30% of the plant length is not sold, but cut off as waste.

Another important parameter for celery plants is the tastiness of the petioles. Commercially it would be a great advantage to provide a tasty celery plant that is smaller in size, such that it corresponds to a smaller portion that is more suitable for consumption by single consumers or small households. Currently the market offers e.g. the tender hearts of normal-sized celery plants to accommodate the consumer's wish for smaller-sized portions of fresh celery. However, this strategy involves the removal of the outer leaves, which requires additional labour. Another possible strategy would be to harvest normal celery plants at an immature stage, and sell them when they are still smaller than normal mature plants. However, such immature celery plants usually have a poor flavour, as many taste components typically only develop during maturation of a vegetable plant, resulting in the full flavour when the crop is mature. Thus, immature celery plants do not taste as well as larger, mature celery plants.

Citation or identification of any document in this application is not an admission that such document is available as prior art to the present invention.

SUMMARY OF THE INVENTION

It is therefore the object of the present invention to provide a new type of celery that remains much smaller in size at the mature harvesting time than celery plants of the prior art which are grown under comparable conditions.

The present invention thus provides a celery plant of the species *Apium graveolens* L. *dulce*, carrying a genetic trait that leads to a shorter petiole and a shorter total plant length at mature harvest stage as compared to a celery plant not carrying the said genetic trait, wherein said genetic trait is obtainable by introgression from a plant grown from seed of which a representative sample was deposited on 24 Nov. 2011 with the NCIMB (NCIMB Ltd., Ferguson Building, Craibstone Estate, Bucksburn, Aberdeen, AB21 9YA Scotland, UK) under accession number NCIMB 41902.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

Deposits

The Deposits with NCIMB Ltd, Ferguson Building, Craibstone Estate, Bucksburn, Aberdeen AB21 9YA, UK, under deposit accession number 41902 were made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent. The deposit will be maintained in the depository for a period of 30 years, or 5 years after the last request, or for the effective life of the patent, whichever is longer, and will be replaced if necessary during that period.

DETAILED DESCRIPTION OF THE INVENTION

Figure 1:
FIG. 1 shows a marketable celery plant of the invention (right) next to a marketable conventional celery plant (left), both at mature harvest stage.

The present invention thus provides a celery plant of the species *Apium graveolens* L. *dulce*, carrying a genetic trait that leads to a shorter petiole and a shorter total plant length at mature harvest stage as compared to a celery plant not carrying the said genetic trait, wherein said genetic trait is obtainable by introgression from a plant grown from seed of which a representative sample was deposited on 24 Nov. 2011 with the NCIMB (NCIMB Ltd., Ferguson Building, Craibstone Estate, Bucksburn, Aberdeen, AB21 9YA Scotland, UK) under accession number NCIMB 41902.

Plants grown from the deposited seeds do not correspond to the definition of a plant variety, as they do not comply with the DUS criteria (Distinct, Uniform, Stable) for all traits.

The plant of the invention may be sold in its entirety, without the need to remove leaves and to create waste prior to sale. The consumer may purchase a maximal portion of the celery plant, which is much smaller and more convenient than a conventionally sized celery plant. Such a small celery plant is ideal for small households or single consumers. It is effectively a "personal celery". When compared to prior art celery plants of the same length that are harvested at an immature stage, the taste of the personal celery is much better. Celery plants of the invention are much smaller when harvested at maturity than prior art celery plants that are harvested at maturity. "Maturity" as used herein is intended to mean that plants of the invention are fully grown and have adult dimensions (i.e. the dimensions of petioles and leaves would not increase further if the plants would be left unharvested for a prolonged period of time). In addition, they may have more, stronger and thicker petioles than immature plants of the same size lacking the trait of the invention. Maturity also may comprise a good taste.

"Introgression" as used herein is intended to mean introduction of a trait into a plant not carrying the trait by means of crossing and selection in the first generation in which the trait becomes visible. For a dominant trait this is in the F1 generation of a cross between a plant with the trait and a plant without the trait. For a recessive trait this is suitably the F2 generation.

The invention relates to a celery plant carrying the genetic determinant as present in the genome of seeds deposited as NCIMB 41902, which determinant is obtainable by introgression from a plant grown from seed, a representative sample of which was deposited with the NCIMB under accession number NCIMB 41902.

It should be noted that if the selection criterion (or criteria) is (or are) clearly defined, the skilled person will be able to identify the descendants that carry the trait in any further generation. With respect to the determinant of the invention that underlies the smaller size of a celery plant of the present invention, plants that carry the determinant may suitably be identified among descendants from a cross between a plant not carrying the determinant, and a plant that does carry the said determinant and of which representative seed was deposited under accession numbers NCIMB 41902, by growing F2 plants from seeds that are the result from the initial cross and a selfing step, and selecting plants showing the desired trait. The said genetic trait is inherited in celery plants in a recessive fashion, as illustrated by example 2.

In one embodiment, the invention relates to a celery plant carrying a genetic trait that leads to a shorter petiole and a shorter total plant length at mature harvest stage as compared to a celery plant not carrying the said genetic trait, wherein said genetic trait is obtainable by:

a) growing plants from seed that was deposited with the NCIMB under accession number NCIMB 41902;
b) crossing the said plant with a plant not showing the trait to obtain an F1 population;
c) selfing plants from the F1 to obtain an F2 population;
d) selecting plants that have shorter petioles and a shorter total plant length at mature harvest stage as being plants of the invention; and
e) optionally repeating steps b) to d)

Plants of the invention are significantly smaller at mature harvest stage than existing celery types (as illustrated by Table 1 and FIG. 1), and in a preferred embodiment they have a good taste. The advantage thereof is that celery plants of the invention—herein referred to as "personal celery plants"—are particularly suited for single consumers or small households, for whom existing celery plants are often too large to be conveniently stored and/or timely consumed. The commercial use of personal celery plants thus leads to less waste during the production, packaging, sale and consumption processes.

Figure 2:
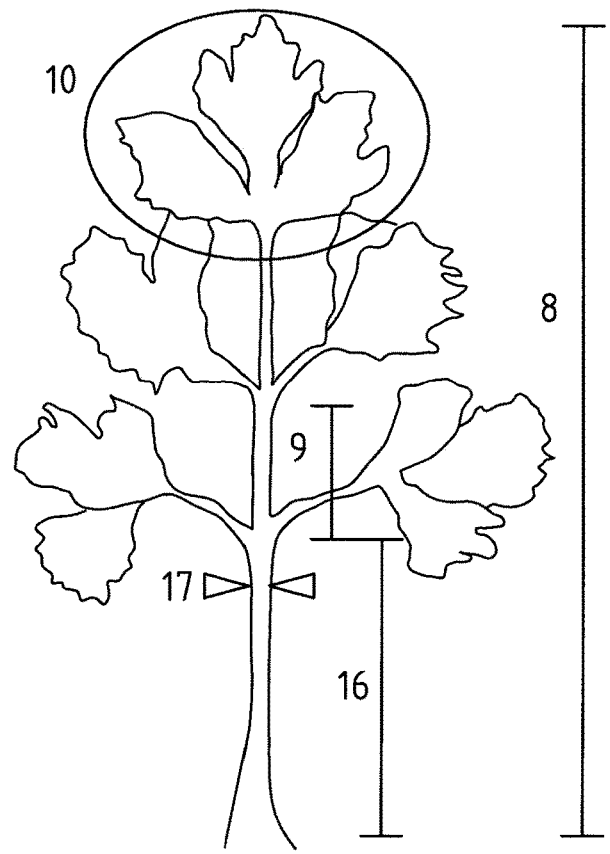
FIG. 2 illustrates the description of a celery leaf according to UPOV TG/82/4.

The "petiole length" is the distance between the leaf base and the first joint as is indicated in FIG. 2 with the numeral 16. The "leaf length" is the total mature leaf length of individual leaves, which is the leaf length at the stage of full leaf expansion, as is indicated in FIG. 2 with the numeral 8. The "total plant length" is the total length of a celery plant prior to the removal of the individual leaves.

Celery plants of the invention are obtainable by crossing a first celery parent plant with a second celery parent plant, wherein one of the parents is a plant grown from seed of which a representative sample was deposited with the NCIMB under deposit accession number NCIMB 41902 or a progeny plant thereof, and selecting for plants that have shorter petioles and a shorter total plant length than a celery plant not carrying the said genetic determinant at maturity.

In this respect the shorter petioles in particular are petioles shorter than 19 cm, preferably shorter than 17 cm, more preferably shorter than 15 cm, even more preferably shorter than 13 cm, even more preferably shorter than 11 cm, most preferably shorter than 9 cm. In this respect the shorter total plant length in particular is a total plant length shorter than 37 cm, preferably shorter than 36 cm or shorter than 35 cm, more preferably shorter than 34 cm or shorter than 33 cm, even more preferably shorter than 32 cm, most preferably shorter than 31 cm.

The petioles of plants of the invention are solid and crunchy at mature harvest stage.

The invention relates to celery plants in all stages of development, even though the characteristics recited above may not be perceivable in all developmental stages. The plant does however contain in all developmental stages the genetic information that leads to the said characteristics in the ready-to-harvest stage.

The invention furthermore relates to a cell of a celery plant as claimed. Such a cell may be either in isolated form, or may be part of the complete celery plant or parts thereof, and then such a cell still constitutes a cell of the invention, because such a cell harbours in its genetic constitution the genetic information that leads to the said characteristics. Each cell of celery plants of the invention carries the genetic information that leads to phenotypic expression of said trait. Such a cell of the invention may also be a regenerable cell that may be used to regenerate a new celery plant of the invention.

The invention also relates to tissue of a plant as claimed. The tissue may be undifferentiated tissue or already differentiated tissue. Undifferentiated tissues are for example stem tips or other meristematic tissues, anthers, petals, pollen. They may be used in micropropagation to obtain new plantlets that are grown into new plants of the invention. The tissue may also be grown from a cell of the invention.

According to a further aspect the invention relates to seeds of a plant as claimed. Although the seeds do not show the characteristics of the celery of the invention, they harbour the genetic information that—when a plant is grown from the seeds—makes this plant a plant of the invention.

The invention also relates to progeny of the plants, cells, tissues and seeds of the invention. Such progeny may in itself be plants, cells, tissues or seeds.

As used herein the word "progeny" is intended to mean the first and all further descendants from a cross with a plant of the invention that shows shorter petioles and a shorter total plant length as compared to a celery plant not carrying the genetic determinant of the invention. Progeny of the invention are descendants of any cross with a plant of the invention that carries the determinant that leads to shorter petioles and a shorter total plant length. In one embodiment, the progeny plant has the novel and inventive combination of morphological and physiological characteristics of the claimed plant, representative seed of which was deposited under NCIMB Accession No. 41902. Such progeny has the same characteristics as claimed for the plant of the invention and may be modified in one or more other characteristics. Such additional modifications are for example effected by mutagenesis or by transformation with a transgene. "Progeny" also encompasses plants that carry the determinant of the invention and that are obtained from other plants or progeny of plants of the invention by vegetative propagation or multiplication.

The invention further relates to seed of the claimed plant and to parts of the plant that are suitable for sexual reproduction. Such parts are for example selected from the group consisting of microspores, pollen, ovaries, ovules, embryo sacs and egg cells. In addition, the invention relates to parts of the plant that are suitable for vegetative reproduction, in particular cuttings, roots, stems, cells, protoplasts.

According to a further aspect of the invention, the invention provides a tissue culture of a plant carrying the genetic determinant of the invention. The tissue culture may comprise regenerable cells. Such tissue culture may be derived from leaves, pollen, embryos, cotyledons, hypocotyls, meristematic cells, roots, root tips, anthers, flowers, seeds and stems. The tissue culture may be regenerated into a plant carrying the genetic determinant of the invention. Suitably a regenerated plant expresses the phenotype of shorter petioles and a shorter total plant length as compared to celery plants not carrying the genetic determinant.

According to another aspect of the present invention, plants are provided that have all of the morphological and physiological characteristics of plants of the invention, representative seed of which was deposited under NCIMB Accession No. 41902, which plants are grown from seeds of the plant of the invention or regenerated from parts thereof, or from a tissue culture.

The term "genetic determinant" as used herein encompasses one or more genes or alleles. These terms are used interchangeably. The "genetic trait" is the trait or characteristic that is conferred by the genetic determinant. The genetic trait may be identified phenotypically. However, also plant stages in which no phenotypic observation is possible do carry the genetic information that leads to the genetic trait. "Trait" or "phenotypic trait" may be used instead of "genetic trait".

The trait of the invention as used herein is referred to as shorter petioles and a shorter total plant length. The mention of this trait is always intended to be compared to a reference. Therefore, as used herein, these are shorter petioles and a shorter total plant length as compared to celery plants not carrying the genetic determinant of the invention.

In the absence of molecular markers, equivalence of genetic determinants may be determined by an allelism test. To perform an allelism test, material that is homozygous for the known determinant is crossed with material that is homozygous for the phenotypic trait to be tested. When no segregation for the trait to be observed is present in the F2 of the cross, the genetic determinants resulting in the phenotypic trait have been proven to be the same. When more than one gene is responsible for a certain trait, and an allelism test is done to determine equivalence, the skilled person doing the test has to ascertain that all relevant genes are present in a homozygous state, in order for the test to work properly.

The invention furthermore relates to hybrid seed and to a method of producing hybrid seed, which may comprise crossing a first parent plant with a second parent plant and harvesting the resulting hybrid seed, wherein said first parent plant and/or said second parent plant is a plant as claimed. Suitably a hybrid plant expresses the phenotype of shorter petioles and a shorter total plant length as compared to celery plants not carrying the genetic determinant. The invention also relates to inbreds and doubled haploids.

In one embodiment, the invention relates to a celery plant which may comprise the trait of the invention, which plant is obtainable by:
  a) crossing a plant, representative seed of which was deposited with the NCIMB under accession number NCIMB 41902, with a plant not showing the trait to obtain an F1 population;
  b) selfing plants from the F1 population to obtain an F2 population;
  c) selecting in said F2 for plants that have the trait of the invention; and
  d) optionally performing one or more additional rounds of selfing or crossing, and subsequently selecting, for the trait.

In one embodiment, the invention relates to celery plants that carry the determinant of the invention and that have acquired said determinant by introduction of the genetic information that is responsible for the trait from a suitable source, either through conventional breeding, or through genetic modification, in particular through cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species, or with a synthetic gene.

In one embodiment, the source from which the genetic information is acquired is formed by plants grown from seeds of which a representative sample was deposited under accession number NCIMB 41902, or from the deposited seeds or sexual or vegetative descendants thereof. The invention also relates to the germplasm of plants of the invention. The germplasm is constituted by all inherited characteristics of an organism and—according to the invention—encompasses at least the trait of the invention.

The invention also relates to the celery petioles (also known as sticks or stalks) that are produced by the plants of the invention. In addition, the invention relates to parts of the leaves and processed products produced from the leaves, and to the entire marketable celery plant without the roots. A marketable celery plant that carries the trait of the invention is much smaller than any marketable celery plant in the prior art, resulting in a niche market for single consumers and small households, a higher convenience, and less waste.

The trait of the invention is recognizable in a celery plant when the petioles are significantly shorter than those of celery plants that are not according to the invention, and when the total plant length is significantly shorter than those of celery plants that are not according to the invention. Significantly shorter or short petioles means, in increasing order of preference, at least 20% shorter, at least 25% shorter, at least 30% shorter, at least 35% shorter, at least 40% shorter, at least 45% shorter, at least 50% shorter, at least 55% shorter, at least 60% shorter, at least 65% shorter, at least 70% shorter, at least 75% shorter, at least 80% shorter at mature harvest stage, when compared to a celery plant not carrying the genetic determinant of the invention. For optimal comparison, celery plants of the invention and other celery plants to which they are compared need to be planted at similar distances (at a similar plant density), because when celery plants grow closely together they usually grow taller than normally. In addition, comparison is suitably made with an isogenic celery plant that differs only from the celery plants of the invention in the absence of the genetic determinant underlying the trait of the invention.

In one aspect the invention relates to a method for production of a celery plant which may comprise shorter petioles and a shorter total plant length, which may comprise:
  a) crossing a plant which may comprise the genetic determinant that leads to expression of shorter petioles and a shorter total plant length with another plant;
  b) selfing the resulting F1 for obtaining F2 plants;
  c) selecting plants which may comprise shorter petioles and/ a shorter total plant length in the F2 generation;
  d) optionally performing one or more additional rounds of selfing or crossing, and subsequently selecting for a plant which may comprise shorter petioles and a shorter total plant length.

It is clear that the parent that provides the trait of the invention is not necessarily a plant grown directly from the deposited seeds. The parent may also be a progeny plant from the deposited seed, or a progeny plant from seeds that are identified to have the trait of the invention by other means.

In one aspect, the invention relates to a method for production of a celery plant which may comprise shorter petioles and a shorter total plant length, which may comprise:
  a) crossing a plant which may comprise the genetic determinant that leads to expression of shorter petioles and a shorter total plant length with another plant;
  b) optionally backcrossing the resulting F1 with the preferred parent;
  c) selecting for plants which may comprise shorter petioles and a shorter total plant length in the F2 generation;
  d) optionally performing one or more additional rounds of selfing or crossing, and subsequently selecting for a plant which may comprise shorter petioles and a shorter total plant length.

The invention additionally provides a method of introducing a desired trait into a celery plant which may comprise shorter petioles and a shorter total plant length, which may comprise:
  a) crossing a celery plant which may comprise shorter petioles and a shorter total plant length, representative seed of which were deposited with the NCIMB under deposit number NCIMB 41902, with a second celery plant that may comprise a desired trait to produce F1 progeny;
  b) selecting an F1 progeny that may comprise shorter petioles and a shorter total plant length and the desired trait;
  c) crossing the selected F1 progeny with either parent, to produce backcross progeny;
  d) selecting backcross progeny which may comprise the desired trait and shorter petioles and a shorter total plant length; and
  e) optionally repeating steps (c) and (d) one or more times in succession to produce selected fourth or higher backcross progeny that may comprise the desired trait and shorter petioles and a shorter total plant length. The invention includes a celery plant produced by this method.

In one embodiment selection for plants which may comprise shorter petioles and a shorter total plant length is done in the F1. Alternatively, selection for the trait of the invention is started in the F2 of a cross or alternatively of a backcross. In another embodiment selection for plants which may comprise shorter petioles and a shorter total plant length is started in the F3 or a later generation.

In one embodiment the plant which may comprise the genetic determinant is a plant of an inbred line, a hybrid, a doubled haploid, or of a segregating population. The invention further provides a method for the production of a celery plant which may comprise shorter petioles and a shorter total plant length by using a doubled haploid generation technique to generate a doubled haploid line, which may comprise the said shorter petioles and a shorter total plant length.

The invention furthermore relates to hybrid seed and to a method for producing hybrid seed, which may comprise crossing a first parent plant with a second parent plant and harvesting the resulting hybrid seed, wherein said first parent plant and/or said second parent plant is a plant of the invention as claimed.

In one embodiment, the invention relates to a method for producing a hybrid celery plant which may comprise crossing a first parent celery plant with a second parent celery plant and harvesting the resulting hybrid celery seed, in which the first parent celery plant and/or the second parent celery plant may comprise shorter petioles and a shorter total plant length.

The invention also relates to a method for the production of a celery plant which may comprise shorter petioles and a shorter total plant length, by using a seed that may comprise a genetic determinant in its genome that leads to shorter petioles and a shorter total plant length for growing the said celery plant. The seeds are suitably seeds of which a representative sample was deposited with the NCIMB under deposit number NCIMB 41902, or seeds that carry the same or essentially the same genetic determinant as the deposited seeds.

The invention also relates to a method for seed production which may comprise growing celery plants from seeds of which a representative sample was deposited with the NCIMB under deposit number NCIMB 41902, allowing the plants to produce seeds, and harvesting those seeds. Production of the seeds is suitably done by crossing or selfing.

In one embodiment, the invention relates to a method for the production of a celery plant which may comprise shorter petioles and a shorter total plant length by using tissue culture. The invention furthermore relates to a method for the production of a celery plant which may comprise shorter petioles and a shorter total plant length by using vegetative reproduction. In another embodiment, the invention relates to a method for the production of a celery plant which may comprise shorter petioles and a shorter total plant length by using a method for genetic modification to introgress shorter petioles and a shorter total plant length into the celery plant. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant. The gene to be introgressed is suitably the gene underlying the genetic determinant of the invention.

The invention also relates to a breeding method for the development of celery plants that may comprise shorter petioles and a shorter total plant length wherein germplasm which may comprise the genetic determinant underlying the shorter petioles and a shorter total plant length of plants of the invention is used. Representative seed of said plant which may comprise the genetic determinant and being representative for the germplasm was deposited with the NCIMB under deposit number NCIMB 41902.

In a further embodiment the invention relates to a method for the production of a celery plant which may comprise shorter petioles and a shorter total plant length wherein progeny or propagation material of a plant which may comprise the genetic determinant conferring said shorter petioles and a shorter total plant length is used as a source to introgress shorter petioles and a shorter total plant length into another celery plant. Representative seed of said plant which may comprise the genetic determinant was deposited with the NCIMB under deposit number NCIMB 41902. The invention provides preferably a celery plant showing shorter petioles and a shorter total plant length, which plant is obtainable by any of the methods herein described.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Characterization of Celery Plants of the Invention

Celery plants of the invention grown from seeds of NCIMB accession 41902 were compared with existing celery plants. Table 1 shows the results of this comparison. FIG. 1 shows a marketable celery plant of the invention (right) next to a marketable conventional celery plant (left), both at their mature harvest stage.

Table 1 shows a comparison of celery plants of the invention (NCIMB 41902) to other celery plants (NCIMB 41513 and three commercial celery varieties: Victoria, Monterey and Tango). For each celery line all sticks and leaf blades of 10 plants were measured. The word "sticks" is herein used as a synonym for "petioles" or "leaf stalks", and the word "stick" is typically used to specify the product after the leaf blades are removed. The total weight of the 10 plants is indicated, along with the total length of each plant, the average length of the sticks from each plant, the average length of the leaf blades from each plant, and the average total leaf length.

The total plant length differs slightly from the average leaf length because it is measured from the tip of the longest leaf, before removal of individual leaves, and hence total plant length is usually slightly longer than the average leaf length. The standard deviation of the stick length (per plant) is also included. The length of the sticks is the distance between the leaf base and the first joint as is indicated in FIG. 2 with the numeral 16. What was measured here is the mature stem length, which is the stem length at the stage of full leaf expansion.

Celery plants of the invention show a smaller mature stem length and a smaller mature stem length distribution than celery plants that do not carry the genetic determinant of the invention. A smaller mature stem length distribution means that the differences between the lengths of the individual stems are small.

The leaf blade is the part of the leaf excluding the petiole, and this part is indicated in FIG. 2 as (length 8) minus (length 16). The word "leaf blade" is synonymous to "subdivided leaf blade" or "blade". The bottom row of the sub-table for each individual celery line lists the average values (total plant length, average stick length and average leaf blade length) for the 10 plants of the celery line that were measured.

It is clear from the results in Table 1 and from FIG. 1 that the celery plants of the invention have significantly shorter petioles, significantly shorter total leaf lengths and a significantly shorter total plant length at mature harvest stage than marketable celery plants at mature harvest stage not carrying the genetic determinant of the invention. Celery plants in the prior art have much longer petioles and leaves than celery plants of the invention. The average petiole (stick) length of prior art celery plants is (25.2±3.5) cm for Victoria, (24.5 cm±3.2) for Monterey and (26.4±4.2) cm for Tango, compared to (9.8±0.8) cm for celery plants of the invention. The average total leaf length (=stick+leaf blade) of prior art celery plants is also much longer than that of celery plants of the present invention: the total leaf length of Victoria is on average 61.6 cm, that of Monterey is 60.3 cm and that of Tango is 56.0 cm, compared to only 28.3 cm for celery plants of the present invention. The average total plant length of prior art celery plants is 72.9 cm for Victoria, 69.6 cm for Monterey and 63.8 cm for Tango, compared to 31.1 cm for celery plants of the present invention.

TABLE 1

| NCIMB 41902 (personal celery) | Total product weight (kg) | # sticks per plant | Total length (cm) | Average stick length (cm) | Average leaf blade length (cm) | st. dev. stick length (cm) | Average total leaf length |
|---|---|---|---|---|---|---|---|
| plant 1 | 4.4 kg | 8 | 33.0 | 9.8 | 20.2 | 0.8 | 30.0 |
| plant 2 | | 10 | 28.0 | 9.4 | 18.1 | 0.8 | 27.5 |

TABLE 1-continued

| NCIMB 41513 | Total product weight (kg) | # sticks per plant | Total length (cm) | Average stick length (cm) | Average leaf blade length (cm) | st. dev. stick length (cm) | Average total leaf length |
|---|---|---|---|---|---|---|---|
| plant 3 | | 11 | 31.0 | 9.4 | 16.9 | 0.8 | 26.3 |
| plant 4 | | 9 | 31.0 | 10.2 | 19.3 | 0.8 | 29.6 |
| plant 5 | | 10 | 30.0 | 9.3 | 18.3 | 0.7 | 27.5 |
| plant 6 | | 9 | 31.5 | 10.2 | 19.4 | 0.8 | 29.6 |
| plant 7 | | 10 | 30.0 | 9.9 | 16.9 | 0.9 | 26.8 |
| plant 8 | | 10 | 30.0 | 9.8 | 16.9 | 0.9 | 26.7 |
| plant 9 | | 8 | 31.0 | 9.9 | 19.6 | 0.7 | 29.5 |
| plant 10 | | 8 | 35.0 | 10.3 | 19.7 | 1.1 | 30.0 |
| Average | | | 31.1 | 9.8 | 18.5 | 0.8 | 28.3 |

| NCIMB 41513 | Total product weight (kg) | # sticks per plant | Total length (cm) | Average stick length (cm) | Average leaf blade length (cm) | st. dev. stick length (cm) | Average total leaf length |
|---|---|---|---|---|---|---|---|
| plant 1 | 5.8 kg | 15 | 39.0 | 22.4 | 16.2 | 1.2 | 38.6 |
| plant 2 | | 18 | 38.5 | 21.5 | 14.7 | 1.0 | 36.2 |
| plant 3 | | 14 | 39.0 | 21.8 | 15.8 | 1.2 | 37.6 |
| plant 4 | | 14 | 42.0 | 23.1 | 17.5 | 1.4 | 40.6 |
| plant 5 | | 13 | 39.0 | 21.4 | 14.5 | 1.3 | 35.9 |
| plant 6 | | 14 | 38.0 | 21.2 | 15.3 | 1.1 | 36.5 |
| plant 7 | | 19 | 41.0 | 22.1 | 15.9 | 1.3 | 37.9 |
| plant 8 | | 15 | 39.0 | 21.7 | 14.5 | 1.3 | 36.2 |
| plant 9 | | 15 | 40.0 | 21.7 | 15.9 | 1.3 | 37.6 |
| plant 10 | | 16 | 39.5 | 20.5 | 14.5 | 2.4 | 35.0 |
| Average | | | 39.5 | 21.7 | 15.5 | 1.3 | 37.2 |

| Victoria | Total product weight (kg) | # sticks per plant | Total length (cm) | Average stick length (cm) | Average leaf blade length (cm) | st. dev. stick length (cm) | Average total leaf length |
|---|---|---|---|---|---|---|---|
| plant 1 | 8.6 kg | 11 | 70.0 | 24.5 | 38.8 | 2.6 | 63.3 |
| plant 2 | | 11 | 72.5 | 23.7 | 35.0 | 3.9 | 58.8 |
| plant 3 | | 11 | 76.0 | 26.3 | 38.5 | 3.3 | 64.8 |
| plant 4 | | 13 | 71.0 | 23.3 | 35.6 | 2.5 | 59.0 |
| plant 5 | | 12 | 71.0 | 25.0 | 34.7 | 3.5 | 59.7 |
| plant 6 | | 13 | 69.0 | 24.5 | 35.8 | 2.7 | 60.3 |
| plant 7 | | 12 | 69.5 | 23.6 | 36.5 | 2.9 | 60.1 |
| plant 8 | | 13 | 75.0 | 27.3 | 37.0 | 4.8 | 64.3 |
| plant 9 | | 13 | 78.0 | 27.0 | 36.3 | 4.8 | 63.3 |
| plant 10 | | 12 | 76.5 | 26.2 | 36.3 | 3.8 | 62.5 |
| Average | | | 72.9 | 25.2 | 36.5 | 3.5 | 61.6 |

| Monterey | Total product weight (kg) | # sticks per plant | Total length (cm) | Average stick length (cm) | Average leaf blade length (cm) | st. dev. stick length (cm) | Average total leaf length |
|---|---|---|---|---|---|---|---|
| plant 1 | 7.3 kg | 10 | 68.0 | 24.0 | 35.1 | 3.1 | 59.1 |
| plant 2 | | 10 | 69.0 | 23.9 | 34.6 | 2.3 | 58.4 |
| plant 3 | | 10 | 70.0 | 24.2 | 35.7 | 3.3 | 59.9 |
| plant 4 | | 10 | 68.0 | 24.2 | 35.7 | 3.2 | 59.9 |
| plant 5 | | 11 | 68.0 | 23.6 | 35.6 | 3.0 | 59.2 |
| plant 6 | | 10 | 73.0 | 25.5 | 35.7 | 3.8 | 61.2 |
| plant 7 | | 10 | 70.0 | 25.1 | 35.5 | 2.8 | 60.6 |
| plant 8 | | 9 | 72.0 | 25.5 | 37.8 | 4.1 | 63.3 |
| plant 9 | | 8 | 69.0 | 24.6 | 34.9 | 3.9 | 59.5 |
| plant 10 | | 9 | 69.0 | 24.2 | 37.8 | 2.9 | 62.0 |
| Average | | | 69.6 | 24.5 | 35.8 | 3.2 | 60.3 |

| Tango | Total product weight (kg) | # sticks per plant | Total length (cm) | Average stick length (cm) | Average leaf blade length (cm) | st. dev. stick length (cm) | Average total leaf length |
|---|---|---|---|---|---|---|---|
| plant 1 | 9.4 kg | 11 | 66.0 | 25.3 | 31.0 | 3.9 | 56.3 |
| plant 2 | | 11 | 67.0 | 25.2 | 30.4 | 4.1 | 55.6 |
| plant 3 | | 11 | 64.0 | 26.3 | 28.5 | 4.0 | 54.8 |
| plant 4 | | 11 | 63.5 | 27.9 | 29.3 | 4.5 | 57.2 |
| plant 5 | | 10 | 66.0 | 26.8 | 31.9 | 3.7 | 58.7 |
| plant 6 | | 12 | 60.0 | 26.7 | 28.5 | 3.4 | 55.1 |
| plant 7 | | 11 | 62.0 | 25.9 | 29.0 | 3.9 | 54.9 |
| plant 8 | | 11 | 60.5 | 26.0 | 27.3 | 5.6 | 53.4 |
| plant 9 | | 10 | 64.0 | 25.2 | 31.6 | 4.7 | 56.8 |
| plant 10 | | 10 | 65.0 | 28.4 | 28.8 | 4.0 | 57.2 |
| Average | | | 63.8 | 26.4 | 29.6 | 4.2 | 56.0 |

The prior art celery plant termed "NCIMB 41513" in Table 1 was deposited with NCIMB on 22 Oct. 2007 and carries a genetic trait (different from the genetic trait of the current invention) that leads to short leaf blades and/or a more uniform distribution of stem lengths as compared to celery plants not carrying the said genetic trait. Plants of NCIMB 41513 have petioles with an average length of 21.7±1.3 cm, compared to 9.8±0.8 cm for celery plants of the present invention, and the plants have an average total length of 39.5 cm, compared to 31.1 cm for celery plants of the present invention.

Example 2

Introduction of the New Trait Into other Celery Plants

Plants of the invention that were deposited under NCIMB accession number 41902 were crossed with normal celery plants. The F2 progeny segregated for plants that showed the same characteristics as the parent plants of NCIMB accession number 41902, and the trait of the invention segregated in a recessive fashion. Further development of these plants resulted in lines with the same trait of the invention, as found in NCIMB accession number 41902.

To further characterize the genetic basis of the trait of the invention, a celery plant of the invention was crossed to a normal celery plant, giving rise to an F1 population that did not phenotypically exhibit the trait of the invention. this observation already demonstrated that the trait of the invention is recessive in nature. An F1 plant from this cross was subsequently backcrossed to a celery plant of the invention (a recurrent parent), which did show the phenotype of the invention. From the progeny of this backcross 179 plants were grown to maturity, and their stick length (petiole length) was measured. It was observed that this population of progeny plants comprised plants of two distinct size categories. The first size category comprised 76 plants with a stick length between 10 cm and 14 cm, and with an average stick length of (12.0±0.9) cm. The second size category comprised the remaining 103 plants, which had a stick length between 19 cm and 32 cm, and an average stick length of (24.1±2.7) cm.

In parallel, selfing of the recurrent parent (which was a celery plant of the invention, as deposited under NCIMB accession number 41902) was performed. From among the progeny of this selfing a population of 46 celery plants was grown to maturity, and measurements revealed that they had stick lengths ranging from 10.5 cm to 13.5 cm, with an average stick length of (12.2±0.7) cm.

It is therefore apparent that the first size category (which may comprise 76 plants of the backcross population of 179 plants) corresponded to plants that phenotypically exhibited the trait of the invention, i.e. they had the same characteristics as the plants of NCIMB accession number 41902. The other size category corresponded to celery plants with a wildtype stick length. The phenotype of the invention was thus observed in 42.5% of the 179 progeny plants of the backcross.

Example 3

Biochemical Measurements

The concentration of various sugars was measured in plants of the invention and in three prior art celery plants. It was found that celery plants of the invention had a higher calculated sweetness index than the other celery varieties. A tasting panel perceived the celery plants of the invention as being particularly tasty, and had a significantly higher liking for celery plants of the invention than for commercial varieties Imperial, Tango and Victoria. Generally, celery plants that are more sweet and more crunchy are more appreciated by consumers.

The "calculated sweetness" or sweetness index is calculated as the sum of the concentrations of sucrose, mannitol, glucose and fructose, each multiplied by a specific sweetness factor. For sucrose this empirical factor is 1.0, for mannitol 0.6, for glucose 0.7, and for fructose 1.7. This index gives a numerical indication of the sweetness of the celery as it is perceived by the average consumer.

TABLE 2

|  | % Brix | mannitol (g/100 ml) | glucose (g/100 ml) | fructose (g/100 ml) | sucrose (g/100 ml) | glc/fru ratio | Sum sugars (g/100 ml) | Sum sugars + mannitol (g/100 ml) | calculated sweetness |
|---|---|---|---|---|---|---|---|---|---|
| personal celery | 3.8 | 0.64 | 0.87 | 0.82 | 0.06 | 1.1 | 1.75 | 2.39 | 2.4 |
| Imperial | 3.6 | 0.63 | 0.74 | 0.68 | 0.00 | 1.1 | 1.42 | 2.05 | 2.1 |
| Monterey | 3.9 | 0.77 | 0.65 | 0.69 | 0.01 | 0.9 | 1.35 | 2.12 | 2.1 |
| Victoria | 3.4 | 0.59 | 0.64 | 0.61 | 0.01 | 1.0 | 1.26 | 1.86 | 1.9 |

Table 2 shows biochemical measurements in celery plants of the invention ("personal celery") in comparison to three commercial celery varieties. All measurements were done on fresh plant material at the mature harvest stage (ready-to-eat sticks). Per celery line nine individual plants were measured, and Table 2 shows average values per celery line. Table 2 illustrates that the calculated sweetness (and the total sugar content) of celery plants of the invention is higher than that of commercial celery varieties.

The invention is further described by the following numbered paragraphs:

1. Celery plant (*Apium graveolens* L. *dulce*) carrying a genetic trait that leads to a shorter petiole and a shorter total plant length at mature harvest stage as compared to a celery plant not carrying the said genetic trait, wherein said genetic trait is as present in the genome of plants grown from seed of which a representative sample was deposited with the NCIMB under accession number NCIMB 41902.

2. A celery plant of paragraph 1, wherein the trait is introgressed from a plant grown from seed of which a representative sample was deposited with the NCIMB under accession number NCIMB 41902.

3. A celery plant according to paragraph 1 or 2, obtainable by:
   growing plants from seed that was deposited with the NCIMB under accession number NCIMB 41902;
   crossing the said plant with a plant not showing the trait to obtain an F1 population;
   selfing plants from the F1 to obtain an F2 population;
   selecting plants that have a shorter petiole and a shorter total plant length at mature harvest stage as being plants of the invention; and
   optionally repeating steps b) to d)

4. Celery plants of any one of paragraphs 1-3, wherein the shorter petioles are in increasing order of preference at least 20% shorter, at least 25% shorter, at least 30% shorter, at least 35% shorter, at least 40% shorter, at least 45% shorter, at least 50% shorter, at least 55% shorter, at least 60% shorter, at least 65% shorter, at least 70% shorter, at least 75% shorter, at least 80% shorter at mature harvest stage, when compared to a celery plant not carrying the genetic determinant of the invention.

5. Celery plants of any one of paragraphs 1-4, wherein at mature harvest stage the shorter petioles are shorter than 19 cm, preferably shorter than 17 cm, more preferably shorter than 15 cm, even more preferably shorter than 13 cm, even more preferably shorter than 11 cm, most preferably shorter than 9 cm.

6. Celery plants of any one of paragraphs 1-5, wherein at mature harvest stage the plants are shorter than 37 cm, preferably shorter than 36 cm or shorter than 35 cm, more preferably shorter than 34 cm or shorter than 33 cm, even more preferably shorter than 32 cm, most preferably shorter than 31 cm.

7. A celery plant of any one of the paragraphs 1-6, wherein the celery plant is a hybrid, doubled haploid, or inbred.

8. Seed of a celery plant of any one of the paragraphs 1-7.

9. Propagation material suitable for producing a plant of any one of the paragraphs 1-9, wherein the propagation material is suitable for sexual reproduction, and is in particular selected from microspores, pollen, ovaries, ovules, embryo sacs and egg cells, or is suitable for vegetative reproduction, and is in particular selected from cuttings, roots, stems, cells, protoplasts, or is suitable for tissue cultures of regenerable cells, and is in particular selected from leaves, pollen, embryos, cotyledon, hypocotyls, meristematic cells, roots, root tips, anthers, flowers, seeds and stems, wherein a plant produced from the propagation material has short petioles and a short total leaf length than a celery plant of the same age not carrying the said genetic determinant.

10. A celery plant produced from the propagation material of paragraph 9, which plant has short petioles and a short total leaf length as compared to a celery plant not carrying the said genetic determinant.

11. Progeny of a plant of any one of the paragraphs 1-8 and 10, wherein the progeny plant has short petioles and a short total leaf length as compared to a celery plant not carrying the said genetic determinant.

12. Food product, comprising the stalks of a celery plant of any one of the paragraphs 1-7, or parts thereof.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for producing an *Apium graveolens* L. *dulce* plant that is shorter than 37 cm at mature harvest stage, comprising:

(a) crossing an *Apium graveolens* L. *dulce* plant grown from seed deposited as NCIMB 41902, or F2progeny thereof that is shorter than 37 cm at mature harvest stage, with another *Apium graveolens* L. *dulce* plant to produce a hybrid progeny;
(b) selfing the hybrid progeny to produce next generation progeny; and
(c) selecting in the next generation progeny or in a subsequent generation for an *Apium graveolens* L. *dulce* that is shorter than 37 cm at mature harvest stage.

2. The method as claimed in claim 1, further comprising the step of
(d) performing one to ten additional rounds of selfing or backcrossing, and subsequently selecting for an *Apium graveolens* L. *dulce* plant that is shorter than 37 cm at mature harvest stage.

3. A method for producing an *Apium graveolens* L. *dulce* F1 variety that is shorter than 37 cm at mature harvest stage comprising crossing of a first parent plant produced by the method of claim 1 with a second, different parent plant produced by the method of claim 1.

* * * * *

UNITED STATES PATENT AND TRADEMARK OFFICE
CERTIFICATE OF CORRECTION

PATENT NO. : 10,492,391 B2
APPLICATION NO. : 15/697622
DATED : December 3, 2019
INVENTOR(S) : Reinier Hendrik Marie Deneer et al.

Page 1 of 1

It is certified that error appears in the above-identified patent and that said Letters Patent is hereby corrected as shown below:

In the Claims

Please amend Claim 1, at Column 15, Line 10 as follows:
1. A method for producing an Apium graveolens L. dulce plant that is shorter than 37 cm at mature harvest stage, comprising: (a) crossing an Apium graveolens L. dulce plant grown from seed deposited as NCIMB 41902, or F2 progeny thereof that is shorter than 37 cm at mature harvest stage, with another Apium graveolens L. dulce plant to produce a hybrid progeny; (b) selfing the hybrid progeny to produce next generation progeny; and (c) selecting in the next generation progeny or in a subsequent generation for an Apium graveolens L. dulce plant that is shorter than 37 cm at mature harvest stage.

Signed and Sealed this
Twenty-first Day of January, 2020

Andrei Iancu
*Director of the United States Patent and Trademark Office*